(12) United States Patent
Faulhaber et al.

(10) Patent No.: US 8,197,483 B2
(45) Date of Patent: Jun. 12, 2012

(54) SURGICAL BONE PUNCH

(75) Inventors: Konstantin Faulhaber, Frittlingen (DE); Peter Schulz, Loeffingen (DE); Markus Nesper, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 761 days.

(21) Appl. No.: 12/072,910

(22) Filed: Feb. 27, 2008

(65) Prior Publication Data

US 2008/0221606 A1 Sep. 11, 2008

(30) Foreign Application Priority Data

Mar. 9, 2007 (DE) .................. 10 2007 011 670

(51) Int. Cl.
*A61B 17/32* (2006.01)
*A61B 17/00* (2006.01)

(52) U.S. Cl. ........................................... 606/83
(58) Field of Classification Search .................. 606/184, 606/83, 180
See application file for complete search history.

(56) References Cited

U.S. PATENT DOCUMENTS

| | | | |
|---|---|---|---|
| 3,752,161 A * | 8/1973 | Bent | 606/184 |
| 3,835,860 A * | 9/1974 | Garretson | 606/79 |
| 4,201,213 A * | 5/1980 | Townsend | 606/174 |
| 4,941,466 A * | 7/1990 | Romano | 606/80 |
| 5,009,661 A * | 4/1991 | Michelson | 606/170 |
| 5,273,519 A * | 12/1993 | Koros et al. | 606/83 |
| 5,653,713 A * | 8/1997 | Michelson | 606/83 |
| 5,681,330 A * | 10/1997 | Hughett et al. | 606/143 |
| 5,782,834 A * | 7/1998 | Lucey et al. | 606/22 |
| 6,142,997 A * | 11/2000 | Michelson | 606/83 |
| 6,575,977 B1 * | 6/2003 | Michelson | 606/83 |
| 7,468,041 B2 * | 12/2008 | Rhodes et al. | 600/564 |
| 7,655,020 B2 * | 2/2010 | Wenzler et al. | 606/185 |
| 2004/0102783 A1 * | 5/2004 | Sutterlin et al. | 606/80 |
| 2004/0186499 A1 | 9/2004 | Michelson | |
| 2006/0111737 A1 * | 5/2006 | Wenzler et al. | 606/184 |

FOREIGN PATENT DOCUMENTS

| | | |
|---|---|---|
| DE | 20 2004 015 643 | 12/2004 |
| DE | 20 2004 017 974 | 1/2005 |
| DE | 102004049242 | * 4/2006 |
| EP | 1 491 155 | 12/2004 |
| WO | 99/08604 | 2/1999 |

* cited by examiner

*Primary Examiner* — Thomas C. Barrett
*Assistant Examiner* — Zade Coley
(74) *Attorney, Agent, or Firm* — Lipsitz & McAllister, LLC

(57) ABSTRACT

In a surgical bone punch having a stationary shaft joined to a handgrip, a slide shaft mounted for longitudinal displacement on this stationary shaft, and a motorized drive in the handgrip for displacement of the slide shaft from a proximal inoperative position to a distal operative position with a preset forward displacement force, in order to control the effective forward displacement force of the slide shaft, it is proposed that the slide shaft carry a stop, which, during displacement of the slide shaft to the operative position, strikes an elastic spring element, which is supported on the stationary shaft, and, during displacement of the slide shaft, counteracts the forward displacement force of the drive.

14 Claims, 5 Drawing Sheets

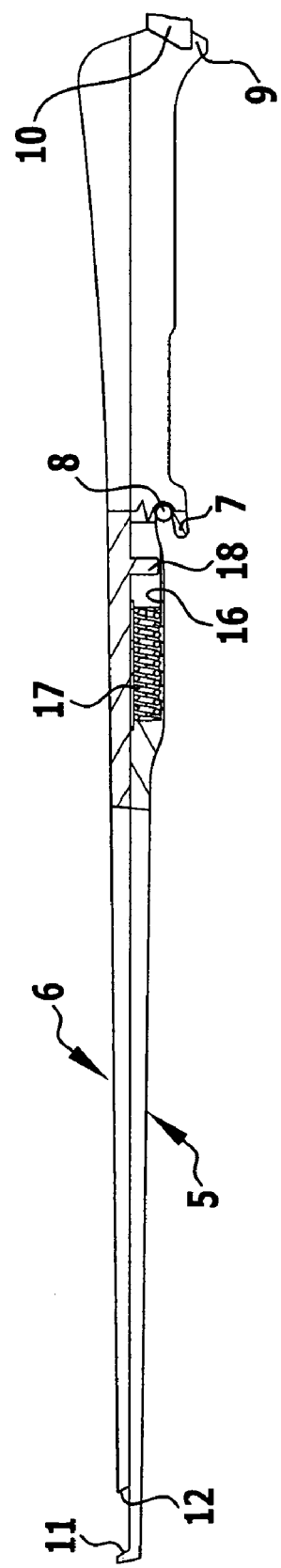

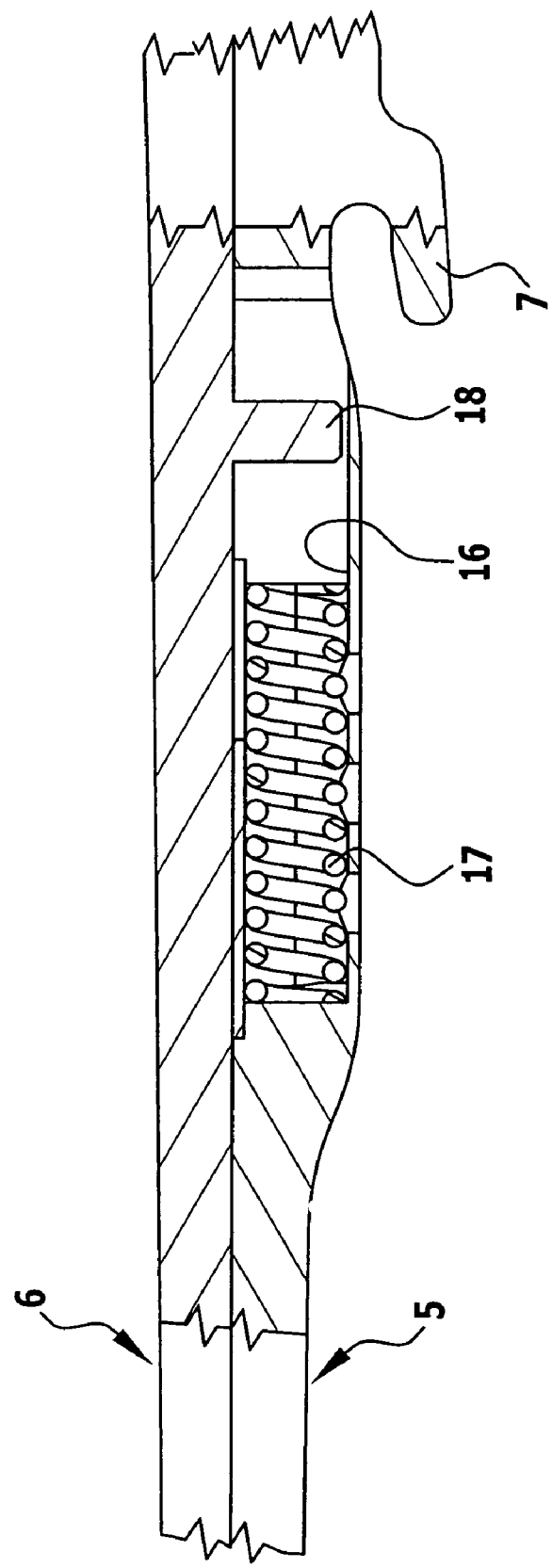

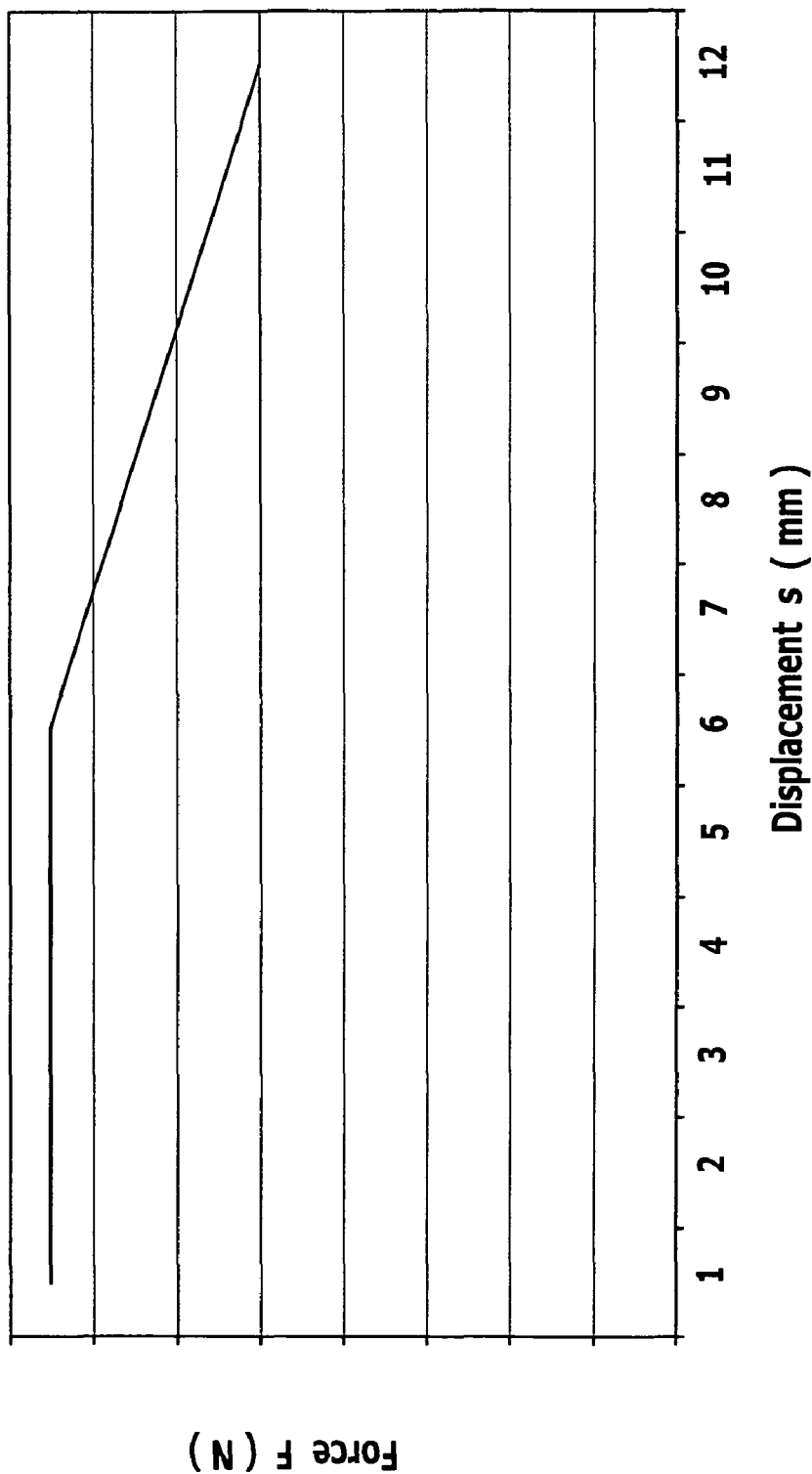

SURGICAL BONE PUNCH

The present disclosure relates to the subject matter disclosed in German application number 10 2007 011 670.7 of Mar. 9, 2007, which is incorporated herein by reference in its entirety and for all purposes.

BACKGROUND OF THE INVENTION

The invention relates to a surgical bone punch having a stationary shaft joined to a handgrip, a slide shaft mounted for longitudinal displacement on this stationary shaft, and a motorized drive in the handgrip for displacement of the slide shaft from a proximal inoperative position to a distal operative position with a preset forward displacement force.

Such a surgical bone punch with a pneumatic drive is known, for example, from DE 20 2004 015 643 U1. The pneumatic drive in the handgrip facilitates the work for the operator and results in reproducible forward displacement forces, which are characteristic of the handgrip, but, on the other hand, do not lend themselves to adaptation to differently dimensioned units consisting of stationary shaft and slide shaft. When such units consisting of stationary shaft and slide shaft, which are differently dimensioned, for example, have bone cutting edges of different width, are used, the cutting forces arising per unit of length of the bone cutting edge can, in the case of narrow cutting edges, therefore, become so great as to result in undesired damage to the cutting edges or undesired injury to the tissue.

In known bone punches, it is, therefore, provided that the forward displacement forces of the drive can be set, for example, by switching over to different intake valves for the pneumatic actuating medium in the handgrip. However, in particular, when exchanging the units consisting of stationary shaft and slide shaft, this is awkward for the operator, and there is the risk that the switching-over will be forgotten and that the bone punch will then be operated with a forward displacement force which is not appropriate for the respectively used unit consisting of stationary shaft and slide shaft.

The object of the invention is to so design a surgical bone punch of the kind described at the outset that the forward displacement force of a unit consisting of stationary shaft and slide shaft automatically adapts to the necessary size, without any change in the forward displacement force supplied by the motorized drive being necessary therefor.

SUMMARY OF THE INVENTION

This object is accomplished, in accordance with the invention, in a surgical bone punch of the kind described at the outset in that the slide shaft carries a stop, which, during displacement of the slide shaft to the operative position, strikes an elastic spring element, which is supported on the stationary shaft, and, during displacement of the slide shaft, counteracts the forward displacement force of the drive.

Due to this force of the elastic spring element counteracting the forward displacement force of the drive, the resulting forward displacement force that acts on the cutting edge of the bone punch is reduced, and by means of appropriately dimensioned elastic spring elements it is possible to select the degree of this reduction, i.e., the reduction can be so selected that the desired forward displacement force occurs for each cutting edge, and the motorized drive continues to always supply the full and constant forward displacement force, but this is reduced to a greater or lesser extent by the elastic spring element.

It is particularly advantageous for the stop of the slide shaft, the elastic spring element and the support of the elastic spring element on the stationary shaft to be so arranged and dimensioned that the elastic spring element, during the displacement of the slide shaft from the inoperative position to the operative position, becomes operative and counteracts the forward displacement force of the motorized drive only after a portion of the path of displacement. As a result, the full forward displacement force of the motorized drive is, at any rate, obtained in the first portion of the forward displacement. A reduction only starts after a portion of the path of displacement and only becomes effective when the cutting edges of the bone punch approach one another and in doing so could become damaged by forward displacement forces that are too high.

Provision may be made in a preferred embodiment for the stationary shaft to have a receiving chamber for an elastic spring element configured as a compression spring, into which receiving chamber a stop arranged on the slide shaft extends and, during displacement of the slide shaft, compresses the compression spring.

It is particularly advantageous for the stationary shaft with the slide shaft to be releasably joined to and detachable from the handgrip. It is thus possible to place different units consisting of stationary shaft and slide shaft on the same handgrip and to thereby adapt the bone punch to the respective conditions.

Provision is made in a particularly preferred embodiment for a set of several exchangeable stationary shafts with slide shafts to be allocated to the bone punch, at least some of these carrying differently dimensioned cutting edges employable with different forward displacement forces, and for each unit consisting of stationary shaft and slide shaft to either not have an elastic spring element counteracting the forward displacement force or to have an elastic spring element with a different spring characteristic, so that the forward displacement force generated by the drive acts on the cutting edge or the cutting edges to the full extent or reduced to an extent which differs in accordance with the respective spring characteristic.

In the case of such an embodiment, the operator can, as required, place different units consisting of stationary shaft and slide shaft on the handgrip, and limitations of the forward displacement forces, which are individually adapted to the dimensions of the respective units, necessarily arise, i.e., each unit undergoes displacement into the operative position with the maximum forward displacement force that is optimal for this unit. This requires no selecting activity or switching-over on the part of the operator. The handgrip can always operate with the same preset forward displacement force.

In particular, it may be provided that the cutting edge or the cutting edges of different units are of different width.

Bone punches may carry one cutting edge on each of the two parts, i.e., on the stationary shaft and on the slide shaft. It is, however, also possible for only one of these parts to carry a cutting edge, and for the other one to carry an abutment surface acting as anvil for tissue, against which the cutting edge is forwardly displaced.

BRIEF DESCRIPTION OF THE DRAWINGS

The following description of preferred embodiments of the invention serves for further explanation in conjunction with the drawings.

FIG. 3 shows a partly sectional view of a unit consisting of stationary shaft and slide shaft with a receiving chamber for a compression spring in the stationary shaft;

FIG. 4 shows an enlarged detail view of the receiving chamber and the compression spring; and FIG. 5 shows a diagram for describing the size of the effective forward displacement force of the slide shaft in dependence upon the path of displacement.

DETAILED DESCRIPTION OF THE INVENTION

Figure 1:
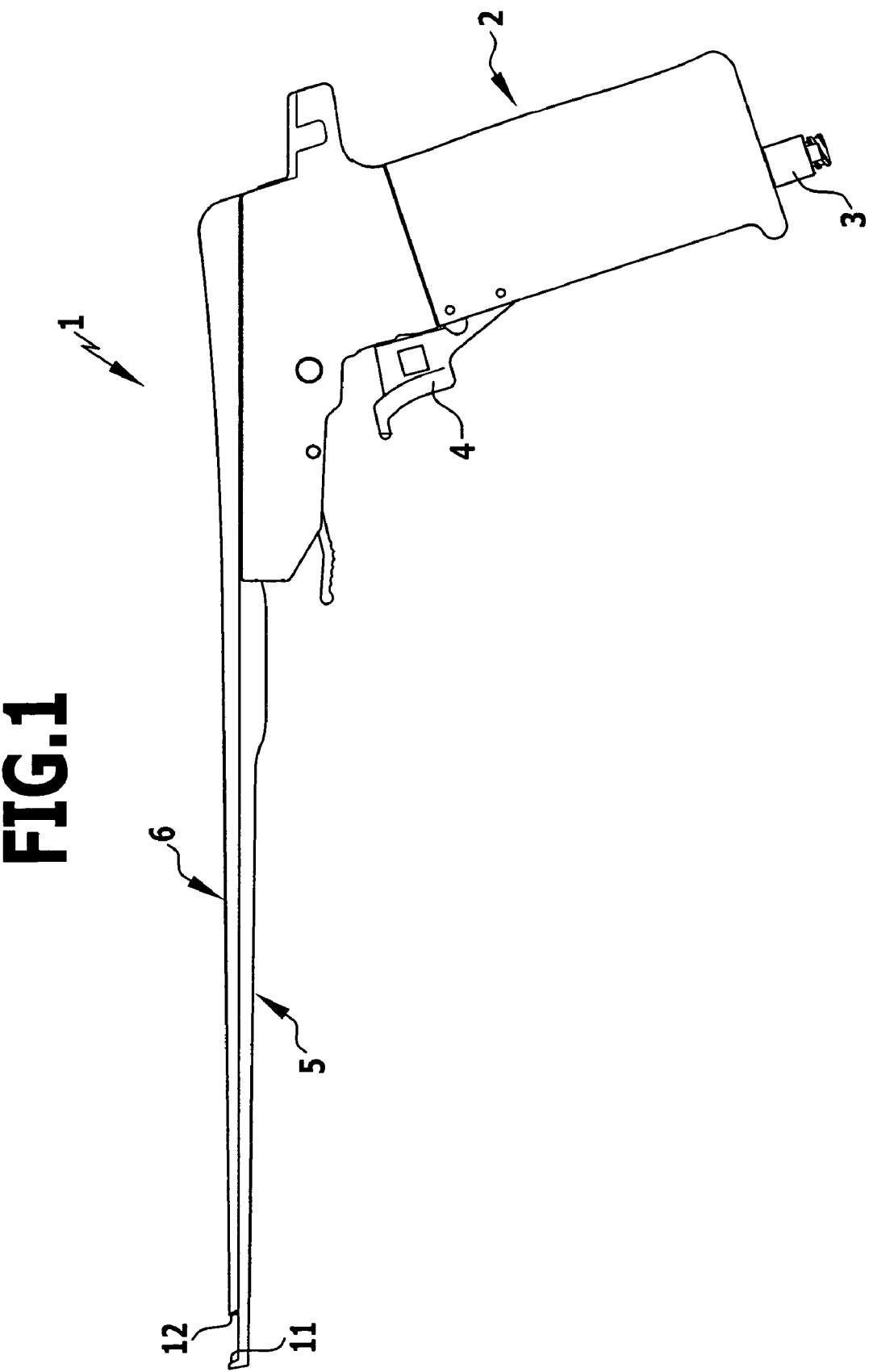
FIG. 1 shows a side view of a bone punch with a handgrip and placed thereon a unit consisting of stationary shaft and slide shaft.

The bone punch 1 shown in the drawings comprises a handgrip 2 with a connection 3 at the lower end thereof, to which a compressed air line, not shown in the drawings, can be connected. Located inside the handgrip 2 is a motorized drive operated by compressed air, which is not shown either, and which can be actuated by an actuating grip 4 which can be pushed into the handgrip.

Figure 2:
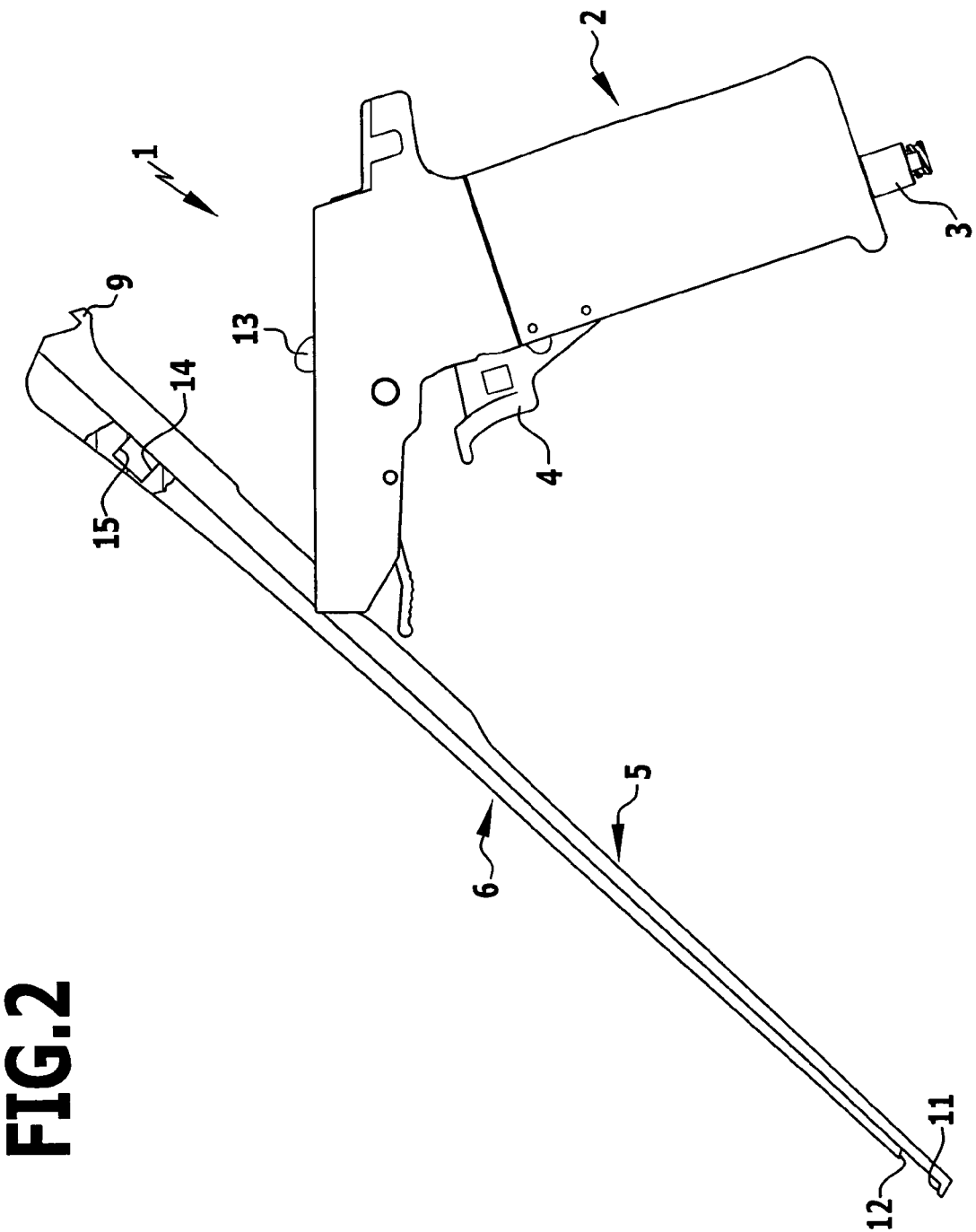
FIG. 2 shows a view similar to FIG. 1 with the unit consisting of stationary shaft and slide shaft in a released position in which it is swiveled out relative to the handgrip.

Releasably held on the handgrip 2 is a unit consisting of a stationary shaft 5 and a slide shaft 6 mounted thereon for displacement in the longitudinal direction. To fix this unit to the handgrip 2, the stationary shaft 5 carries at its lower end a retaining hook 7, which is open towards the distal, front end of the stationary shaft 5 and engages around a retaining bar 8 at the upper distal end of the handgrip 2. This retaining bar 8 forms a swivel axis for the stationary shaft 5. The stationary shaft 5 can be swiveled around this swivel axis between a released position in which it extends at an incline to the upper side of the handgrip 2 (FIG. 2), and a fixed position in which the stationary shaft 5 extends parallel to the upper side of the handgrip 2 (FIG. 1). In the fixed position, the stationary shaft 5, with a retaining nose 9 arranged at its lower, proximal end, engages a detent projection 10 at the upper, proximal end of the handgrip 2, so that the stationary shaft 5 is thereby fixed on the handgrip 2. The detent projection 10 can be retracted by suitable means, not shown in greater detail in the drawings, so that the retaining nose 9 is released. In this way, the unit consisting of stationary shaft 5 and slide shaft 6 can be easily taken off the handgrip 2 and replaced by another unit.

The stationary shaft 5 is a rigid shaft, which extends from the handgrip 2 to its distal end and carries at its distal end a stop face 11 pointing upwards at an incline. Mounted on the stationary shaft 5 and guided for longitudinal displacement in a guide is the slide shaft 6, which also extends substantially over the entire length of the stationary shaft 5 and terminates at its distal end in a cutting edge 12, which is located opposite the stop face 11. It is possible to cut through tissue located between the cutting edge 12 and the stop face 11, for example, bone material, on bringing the cutting edge 12 up to the stop face 11.

The displacement of the slide shaft 6 along the stationary shaft 5 is brought about via the motorized drive inside the handgrip 2. This motorized drive displaces a driver 13 in the direction of the slide shaft and back. The driver 13 projects upwards slightly above the upper side of the handgrip 2 and, extending from below through the stationary shaft, engages around the slide shaft 6. This slide shaft 6 carries immediately in front of and immediately behind the driver 13 lateral stop faces 14, 15, which abut on the driver 13 and thereby take the slide shaft 6 along with them as the driver 13 moves forwards and backwards. On pressing the actuating grip 4 and actuating the motorized drive, the slide shaft 6 is displaced in the distal direction. On terminating the actuation, the driver 13 is moved back into the initial position, either by the motorized drive or by suitable spring means in the handgrip, so that the slide shaft is retracted into the proximal initial position again.

Arranged in the stationary shaft 5 in front of the retaining hook 7 is an upwardly open receiving chamber 16, in which a helical spring 17 is placed. The helical spring 17 is supported at the distal end of the receiving chamber 16 on the stationary shaft 5, and it is shorter than the receiving chamber 16, so that it only fills out the distal portion of the receiving chamber 16. For example, the helical spring 17 may be half as long as the receiving chamber.

A projection 18 arranged at the lower end of the slide shaft 6 extends into that portion of the receiving chamber 16 which is not filled out by the helical spring 17. On displacing the slide shaft 6 forwards out of the inoperative position into the distal operative position, the projection 18 first passes through that portion of the receiving chamber which is free from the helical spring 17 and then enters into abutment on the helical spring 17. On further displacement in the distal direction, the helical spring 17 is compressed by this projection 18 and upon progressive displacement in the distal direction thereby exerts an increasing resetting force on the slide shaft.

The forward displacement force of the motorized drive remains substantially constant during the entire forward displacement, so that the forward displacement force effectively displacing the slide shaft 6 in the distal direction at the beginning of the forward displacement corresponds to the forward displacement force of the motorized drive and then continuously decreases after the driver 13 enters into abutment on the helical spring 17. The course of this force is shown in FIG. 5.

The characteristic of the helical spring 17 placed in the receiving chamber 16 is adapted to the dimensions of the respective unit consisting of stationary shaft 5 and slide shaft 6. For example, in the case of a very narrow cutting edge, for example, a cutting edge of 2 millimeters in width, a relatively strong helical spring 17 is inserted, in the case of a wider cutting edge, for example, a cutting edge of 5 millimeters in width, a considerably weaker helical spring 17, so that the forward displacement force effectively made available at the cutting edge increases with the width of the cutting edge.

In the extreme case, insertion of a helical spring 17 can be dispensed with entirely, for example, in the case of very wide cutting edges that have a width of 6 millimeters or so.

In this way, each unit consisting of stationary shaft and slide shaft itself controls the forward displacement forces effectively occurring at the cutting edge, although the forward displacement force supplied by the handgrip and the motorized drive is always identical. The operator is relieved of the task of adjusting the forward displacement force and, in addition, is unable to make a mistake.

It is possible to allocate to a handgrip 2 a number of units consisting of stationary shaft and slide shaft, which have different dimensions and hence also helical springs 17 of different strength. Owing to the releasable attachment of the units to the handgrip 2, these units can be easily exchanged and they themselves select the course of the forward displacement force respectively required for the unit by virtue of the respectively inserted helical spring 17.

The invention claimed is:

1. Surgical bone punch, comprising:
a stationary shaft joined to a handgrip,
a slide shaft mounted for longitudinal displacement on the stationary shaft, and
a motorized drive in the handgrip for displacement of the slide shaft from a proximal inoperative position to a distal operative position with a preset forward displacement force, wherein:
the slide shaft carries a stop, which, during displacement of the slide shaft to the operative position, strikes an elastic spring element, which is supported on the stationary shaft, and, during displacement of the slide shaft, counteracts the forward displacement force of the drive, the stop does not contact the elastic spring element with a compressive force in a first portion of a path of displacement; and the stop of the slide shaft, the elastic spring element and a support of the elastic spring element on the stationary shaft are so arranged and dimensioned that the elastic spring element, during the displacement of the slide shaft from the inoperative position to the operative position, becomes operative and counteracts the forward displacement force only during displacement of the slide shaft along a second portion of the path of the displacement.

2. Bone punch in accordance with claim 1, wherein the stationary shaft comprises a receiving chamber for the elastic spring element configured as a compression spring, into which receiving chamber the stop arranged on the slide shaft extends and, during forward displacement of the slide shaft, compresses the elastic spring element.

3. Bone punch in accordance with claim 1, wherein the stationary shaft with the slide shaft is releasably joined to and detachable from the handgrip.

4. Bone punch in accordance with claim 2, wherein the stationary shaft with the slide shaft is releasably joined to and detachable from the handgrip.

5. Bone punch in accordance with claim 3, wherein:
a set of several exchangeable stationary shafts with slide shafts is allocated to the bone punch, at least some of these carrying differently dimensioned cutting edges employable with different forward displacement forces, and each unit comprising one stationary shaft and corresponding slide shaft either does not have an elastic spring element counteracting the forward displacement force or has an elastic spring element with a different spring characteristic, so that the forward displacement force generated by the drive acts on the cutting edge or on the cutting edges to the full extent or to a reduced extent which differs in accordance with the respective spring characteristic.

6. Bone punch in accordance with claim 4, wherein:
a set of several exchangeable stationary shafts with slide shafts is allocated to the bone punch, at least some of these carrying differently dimensioned cutting edges employable with different forward displacement forces, and each unit comprising one stationary shaft and corresponding slide shaft either does not have an elastic spring element counteracting the forward displacement force or has an elastic spring element with a different spring characteristic, so that the forward displacement force generated by the drive acts on the cutting edge or on the cutting edges to the full extent or to a reduced extent which differs in accordance with the respective spring characteristic.

7. Bone punch in accordance with claim 5, wherein the cutting edge or the cutting edges of the different units are of different width.

8. Bone punch in accordance with claim 6, wherein the cutting edge or the cutting edges of the different units are of different width.

9. Surgical bone punch, comprising:
a stationary shaft joined to a handgrip,
a slide shaft mounted for longitudinal displacement on the stationary shaft,
an elastic spring element supported by the stationary shaft,
a motorized drive in the handgrip for the displacement of the slide shaft along a path from a proximal inoperative position to a distal operative position with a preset forward displacement force, and
a stop disposed on the slide shaft which, after displacement of the slide shaft over a first portion of the path in which the stop does not contact the elastic spring element with a compressive force, only contacts the elastic spring element with a compressive force in a second portion of the path,
wherein the elastic spring element counteracts the forward displacement force of the drive when contacted by the stop only during displacement of the slide shaft along the second portion of the path.

10. Bone punch in accordance with claim 9, wherein the stationary shaft with the slide shaft is releasably joined to and detachable from the handgrip.

11. Bone punch in accordance with claim 10, wherein:
a set of several exchangeable stationary shafts with slide shafts is allocated to the bone punch, at least some of these carrying differently dimensioned cutting edges employable with different forward displacement forces, and each unit comprising one stationary shaft and corresponding slide shaft either does not have an elastic spring element counteracting the forward displacement force or has an elastic spring element with a different spring characteristic, so that the forward displacement force generated by the drive acts on the cutting edge or on the cutting edges to the full extent or to a reduced extent which differs in accordance with the respective spring characteristic.

12. Bone punch in accordance with claim 11, wherein the cutting edge or the cutting edges of the different units are of different width.

13. Bone punch in accordance with claim 1, wherein:
a longitudinal axis of the elastic spring element is parallel to a longitudinal axis of the slide shaft.

14. Bone punch in accordance with claim 9, wherein:
a longitudinal axis of the elastic spring element is parallel to a longitudinal axis of the slide shaft.

* * * * *